(12) United States Patent
Lee et al.

(10) Patent No.: US 10,821,192 B2
(45) Date of Patent: Nov. 3, 2020

(54) MACROPHAGE-TARGETING NANOASSEMBLY AND ANTI-INFLAMMATORY COMPOSITION CONTAINING SAME

(71) Applicants: Korea National University of Transportation Industry-Academic Cooperation Foundation, Chungju-si (KR); Industry Foundation of Chonnam National University, Gwangju (KR)

(72) Inventors: Yong Kyu Lee, Chungju-si (KR); Vishnu Revuri, Chungju-si (KR); In-Kyu Park, Gwangju (KR); Santhosh Kalash Rajendrakumar, Gwangju (KR)

(73) Assignees: Korea National University of Transportation Industry-Academic Cooperation Foundation, Chungju-si (KR); Industry Foundation of Chonnam National University, Gwangju (KR)

( * ) Notice: Subject to any disclaimer, the term of this patent is extended or adjusted under 35 U.S.C. 154(b) by 0 days.

(21) Appl. No.: 16/380,465

(22) Filed: Apr. 10, 2019

(65) Prior Publication Data
US 2020/0114021 A1 Apr. 16, 2020

(51) Int. Cl.
*A61K 47/69* (2017.01)
*A61P 29/00* (2006.01)

(52) U.S. Cl.
CPC .......... *A61K 47/6931* (2017.08); *A61P 29/00* (2018.01)

(58) Field of Classification Search
CPC ................................ A61K 47/69; A61P 29/00
See application file for complete search history.

(56) References Cited

PUBLICATIONS

Kalash et al. (Nano Letters (2018)18, 6417-6426 Published Sep. 24, 2018).*
Wang et al. Chinese ChemicalLetters29(2018)1685-1688.*
Liu et al. Analyst, 2012, 137, 4552.*

\* cited by examiner

*Primary Examiner* — Shirley V Gembeh
(74) *Attorney, Agent, or Firm* — Mintz Levin Cohn Ferris Glovsky and Popeo, P.C.

(57) ABSTRACT

Disclosed are a macrophage-targeting nanoassembly capable of efficiently removing reactive oxygen species to minimize the occurrence of inflammation and an anti-inflammatory composition containing the same.

9 Claims, 6 Drawing Sheets

MACROPHAGE-TARGETING NANOASSEMBLY AND ANTI-INFLAMMATORY COMPOSITION CONTAINING SAME

CROSS-REFERENCE TO RELATED APPLICATION

This application claims priority to Korean Application No. 10-2018-0122126 filed on Oct. 12, 2018, which is incorporated herein by reference.

TECHNICAL FIELD

Various embodiments of the present disclosure relates to a macrophage-targeting nanoassembly and an anti-inflammatory composition containing the same.

BACKGROUND ART

Approximately 90% of modern human diseases are known to be associated with reactive oxygen species, and typical diseases thereof include chronic inflammation, cancer, stroke, myocardial infarction, and the other like, which are common around us. An appropriate amount of reactive oxygen species in our body performs an immune function of protecting against bacteria or viruses, but the over-production of reactive oxygen species causes not only cancer, but also various diseases and aging due to deterioration in physiological function. In particular, hydroxy radicals, which are a type of reactive oxygen species and derived from hydrogen peroxide, are known to cause strong cytotoxicity.

In addition, oxidative stress due to reactive oxygen species is known to be one of the main causes of Parkinson's disease and Alzheimer's disease, and therefore, the efficient elimination of reactive oxygen species is a major issue at present.

SUMMARY

The present disclosure has been made in order to solve the above-mentioned problems in the prior art. Various embodiments of the present disclosure are to provide a macrophage-targeting nanoassembly capable of efficiently removing reactive oxygen species to minimize the occurrence of inflammation and an anti-inflammatory composition containing the same.

A macrophage-targeting nanoassembly of the present disclosure may be a mannosylated polymeric albumin manganese dioxide (mSPAM) nanoassembly.

The macrophage-targeting nanoassembly of the present disclosure may be famed by synthesis of a bovine serum albumin nanoparticle coated with manganese dioxide (BSA-$MnO_2$, BM) and mannosylated disulfide cross-linked polyethylenimine (ssPEI-Mannose, mSP).

The macrophage-targeting nanoassembly of the present disclosure can suppress inflammation inducing factors by selectively removing hydrogen peroxide ($H_2O_2$).

The macrophage-targeting nanoassembly of the present disclosure can alleviate LPS-induced endotoxemia and neuritis.

An anti-inflammatory composition of the present disclosure may contain a mannosylated polymeric albumin manganese dioxide nanoassembly.

The nanoassembly contained in the anti-inflammatory composition of the present disclosure may be famed through the synthesis of a bovine serum albumin nanoparticle coated with manganese dioxide (BSA-$MnO_2$, BM) and mannosylated disulfide cross-linked polyethylenimine (ssPEI-Mannose, mSP).

The anti-inflammatory composition of the present disclosure can suppress inflammation inducing factors by selectively removing hydrogen peroxide ($H_2O_2$).

The anti-inflammatory composition of the present disclosure can alleviate LPS-induced endotoxemia and neuritis.

According to the present disclosure, the macrophage-targeting nanoassembly and the anti-inflammatory composition containing the same of the present disclosure can catalyze the degradation of hydrogen peroxide ($H_2O_2$) involved in hyper-activation of inflammatory immune cells. The highly stable mSPAM nanoassembly of the present disclosure can inhibit the expression of HIF1α and the expression of pro-inflammatory cytokines, such as TNFα and IL-6, by removing $H_2O_2$ in LPS-induced macrophages. The mSPAM nanoassembly and the inflammatory composition comprising the same can serve as an anti-inflammatory agent and can be successfully applied to even various inflammation-related diseases.

Meanwhile, existing metallic nanomaterials cause unnecessary immune activation to result in undesirable long-team accumulation and residence in organ systems in the human body, whereas $MnO_2$ nanomaterials are degraded into $Mn^{2+}$ ions by catalytic action, leading to a reduced residence time in the body and a minimal exposure to innate immune cells. Furthermore, the macrophage-targeting nanoassembly of the present disclosure has improved biocompatibility since serum albumin is used in the production of $MnO_2$ nanoparticles, leading to high stability and low cytotoxicity. In this way, the mSPAM nanoassembly is formed by an electrostatic interaction between a cationic polymer and an anionic protein-metal hybrid, thereby preventing the discharge of toxic byproducts generated due to covalently linked polymer degradation, and thus is very suitable for clinical environments.

Furthermore, the present disclosure established that the reduction of pro-inflammatory cytokines by the mSPAM nanoassembly additionally prevented the activation of microglial cells in the brain, thus ultimately improving animal cognitive ability. Accordingly, the macrophage-targeting nanoassembly and the anti-inflammatory composition containing the same of the present disclosure can also be applied to the treatment of brain cognitive disorder caused by continuous inflammation response.

BRIEF DESCRIPTION OF THE DRAWINGS

The above and other aspects, features and advantages of the present disclosure will be more apparent from the following detailed description taken in conjunction with the accompanying drawings, in which.

DETAILED DESCRIPTION

Hereinafter, various embodiments of the present disclosure are described. It should be understood that embodiments and terminologies used herein are not intended to limit the technology described in the present disclosure to particular forms of embodiments, but to cover various modifications, equivalents, and/or alternatives of corresponding embodiments.

Figure 1:
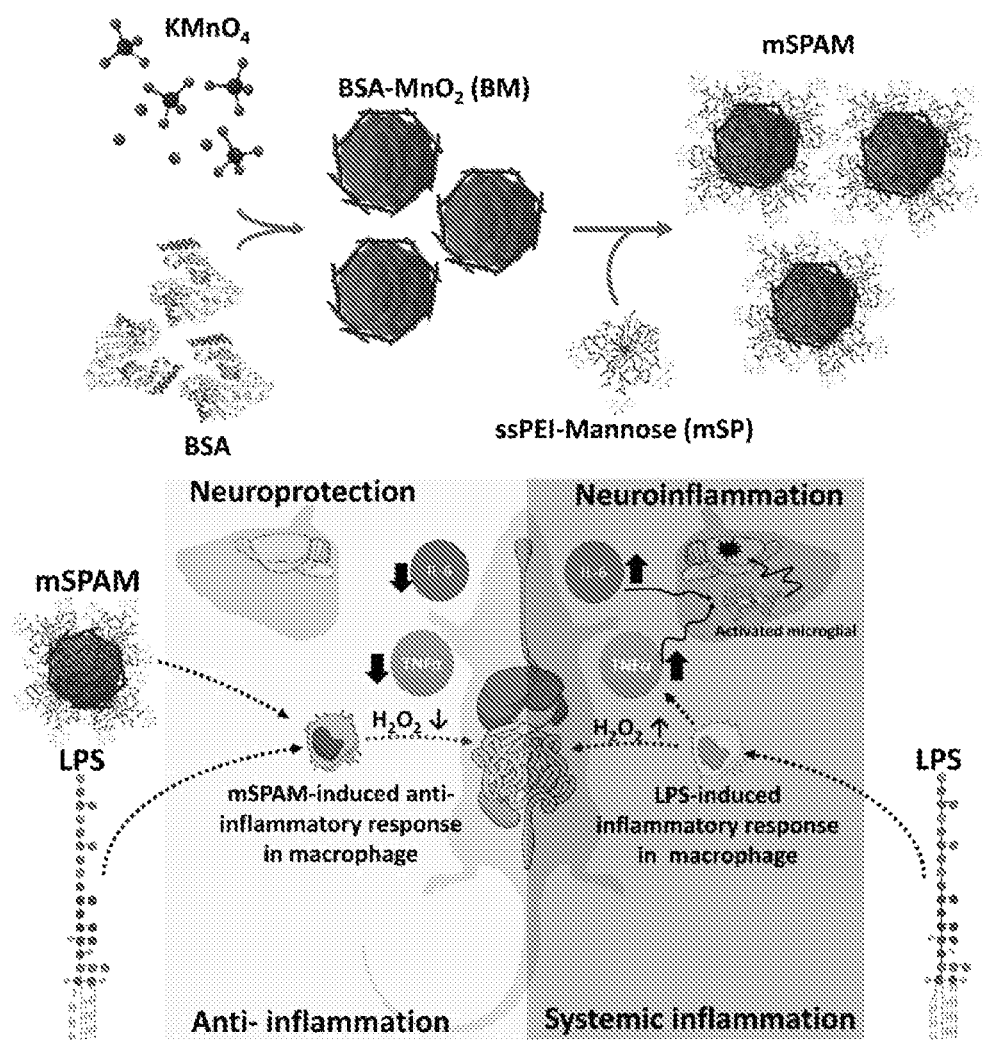
FIG. 1 shows a schematic representation on formulation of mSPAM nanoassembly and a schematic representation on and anti-inflammation induction mechanism in LPS-induced sepsis mouse models.

Referring to the top section of FIG. 1, the mSPAM nanoassembly of the present disclosure can be synthesized by facile one-step electrostatic interaction approach using BSA-MnO$_2$ (BM) nanoparticle complexed with cationic ssPEI-Mannose (mSP) polymer.

Here, BM can be synthesized by coating bovine serum albumin (BSA) with manganese dioxide.

The disulfide bound poly ethylene imine (ssPEI) is initially synthesized followed by conjugating isothiocyanate functionalized mannose with amine groups of ssPEI to synthesize mannosylated ssPEI (mSP).

Referring to the bottom-right section of FIG. 1, LPS induces H$_2$O$_2$ production in macrophage cells, thereby causing secretion of pro-inflammatory cytokines, such as TNFα and IL-6. The secreted pro-inflammatory cytokines activate microglial cells, leading to neural cell death and neuroinflammation.

Referring to the bottom-left section of FIG. 1, mSPAM nanoassembly suppresses H$_2$O$_2$ in macrophages cells to induce the inhibition of pro-inflammatory cytokines, thus indirectly providing neuroprotection.

Hereinafter, the present disclosure will be described in detail with reference to examples and experimental examples.

However, the following examples and experimental examples are merely for illustrating the present disclosure, and the present disclosure is not limited by the following examples and experimental examples.

EXAMPLES

1. Synthesis of BSA-MnO$_2$ Nanoparticles (BM)

Bovine serum albumin (BSA) nanoparticles coated with manganese dioxide (BSA-MnO$_2$, BM) were prepared. Specifically, 800 μg of KMnO$_4$ was mixed with BSA (2 mg/ml), and incubated at room temperature for 12 h. Later, the nanoparticles were dialyzed and lyophilized or directly used for the experiment.

2. Synthesis of ssPEI-Mannose (mSP) Polymer

BPEI-SH and disulfide cross-linked polyethylene imine (PEI) were synthesized. Specifically, 5 g of BPEI1.2K in 5 ml distilled water (DW) was adjusted to pH 7.2 by adding 0.1 N HCl, and then freeze dried for 2 days to remove the water. Then, the obtained yellow solid was dissolved in 150 ml methanol and purged with nitrogen for 10 min. Propylene sulfide in an amount of 5 molar time's excess to BPEI amount was added and then stirred for 24 hr at 60□. Later, the solution was dried by rotor evaporation under reduced pressure. The dried solid was mixed with methanol, followed by precipitation in cold diethyl ether twice. The thiol group content was measure by Ellman's Method. For disulfide cross-linked PEI, 1 g of SH-BPEI in 100 ml of DMSO was stirred for 48 h at room temperature. Then, the resulting material was dialyzed in 3500 MWCO membrane for three days against water and later lyophilized. The chemical structure was confirmed by 1H NMR (in D$_2$O, 300 MHz). Mannose-functionalized isocyanate (Mannose-ITC) was mixed with a known amount of ssPEI at different amine molar ratio (5%, 10%, and 15%) in the presence of DMSO for 48 h. Then, the mixture was dialyzed against water and lyophilized. NMR analysis was performed in D$_2$O solvent.

3. Synthesis of Mannosylated Polymeric Albumin Manganese Dioxide (mSPAM) Nanoassembly Different concentrations of mSP were added to 1 mL of BM (2.8 mg/mL). The samples were then vortexed for 30 s, followed by incubation at room temperature for 30 min. Similarly, SPAM was also synthesized in the same manner using ssPEI.

Experimental Example 1: Physiochemical Characterization of mSPAM Nanoassembly and its Toxicity Profile Thereof In FIG. 2a, the left image is a TEM image of BM, and the right image is a TEM image of mSPAM nanoassembly. It was confirmed through the left image in FIG. 2a that BSA was covered with MnO$_2$ and that BM had the spherical morphology of a nanomaterial. In addition, it was confirmed from the right image in FIG. 2a that mSPAM nanoassembly had spherical morphology. It was confirmed through FIG. 2b that the mSPAM nanoassembly had an average size of 97 nm and a surface charge of +17.8±3 mV when mSP:BM is 1:2 (w/w).

Figure 2:
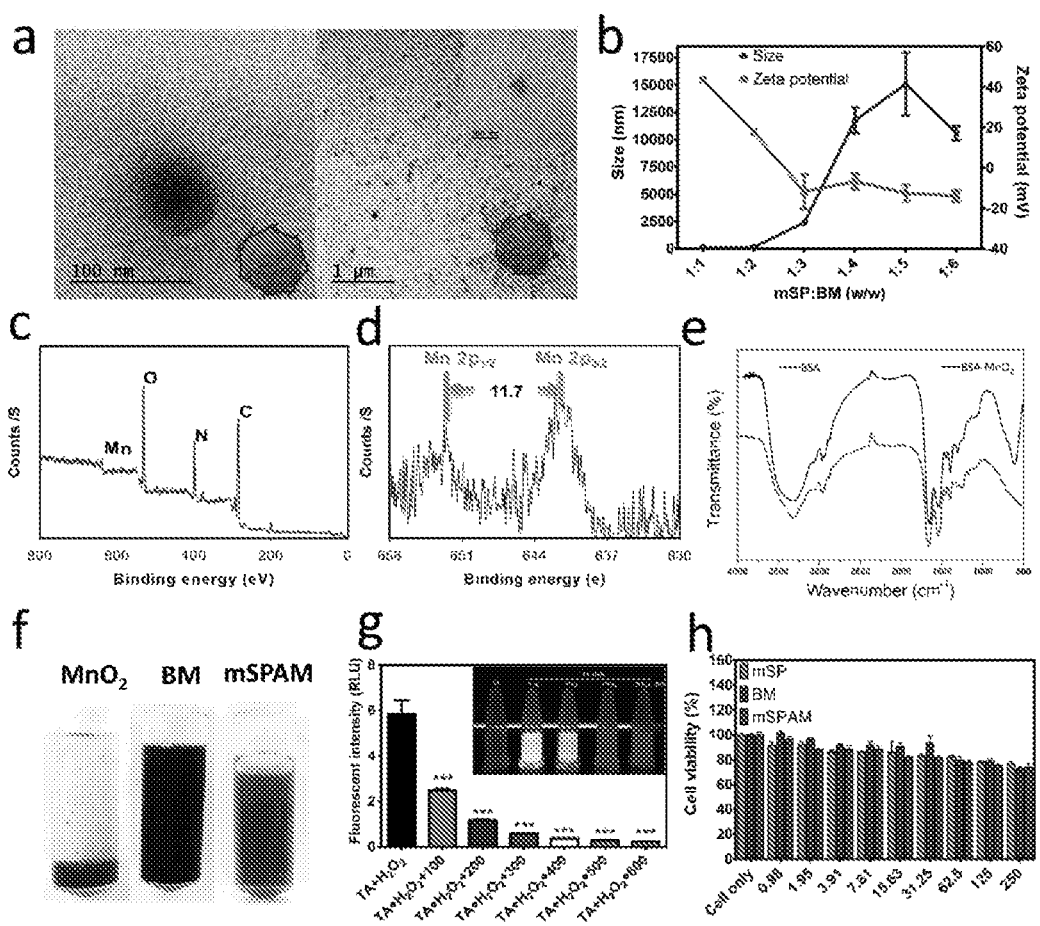
FIG. 2 shows TEM images of BM and mSPAM (a); a plot of hydrodynamic size and ζ potential of mSPAM nanoassembly formulation at different weight ratios (mSP:BM) (b); XPS of mSPAM nanoassembly (c and d); FTIR spectra of BM (e); stability evaluation results of $MnO_2$, BM, and mSPAM (f); $H_2O_2$ scavenging assay results using terephthalic acid (g); and cell viability of RAW 264.7 cell line treated with mSPAM nanoassembly (h)

Referring to FIG. 2c, XPS of mSPAM nanoassembly confined the presence of manganese atom along with carbon, oxygen, and nitrogen atoms in the mSPAM nanoassembly. Referring to FIG. 2d, the higher-resolution manganese spectra confirmed the presence of Mn $2p_{1/2}$ and Mn $2p_{3/2}$. Moreover, the spin-orbital splitting distance between the Mn $2p_{1/2}$ and Mn $2p_{3/2}$ peaks was approximately 11.7 eV, which indicates the oxidation state of manganese ion ($Mn^{2+}$) in the mSPAM nanoassembly.

Referring to FIG. 2e, FTIR spectra confirmed the presence of $MnO_2$ in the synthesized mSPAM nanoassembly. The peak at 540 $cm^{-1}$ showed the presence of Mn in the BM nanoparticle, and the peak shift near 1400 $cm^{-1}$ indicated the strong interaction between the carboxyl $COO^-$ groups of BSA and the manganese ions.

Referring to FIG. 2f, the stability of $MnO_2$ was greatly improved after BSA coating. Moreover, the coating of mSP on BM nanoparticle showed negligible effects on the stability of the mSPAM nanoassembly. These characterizations confirmed that the synthesized nanoassembly is stable in biological environments.

$H_2O_2$ triggers the generation of free radicals responsible for the initiation of immune activation. Therefore, terephthalic acid (TA) was used as a $H_2O_2$-sensing fluorescent probe to investigate the effect of mSPAM nanoassembly of reducing $H_2O_2$-mediated free radical production. As shown in FIG. 2g, the fluorescence of TA was significantly increased in the presence of $H_2O_2$. However, after the addition of mSPAM nanoassembly, the fluorescence of TA in the presence of $H_2O_2$ was significantly reduced. Moreover, the fluorescence intensity of TA was further reduced with increasing concentration of mSPAM nanoassembly. Since the mSPAM assembly catalytically reduced or degraded $H_2O_2$, the formation of free radicals from $H_2O_2$ was clearly inhibited. This result indicated that mSPAM can effectively quench the production of $H_2O_2$-mediated free radicals.

Before considering biomedical applications of mSPAM, toxicology evaluation of the mSPAM nanoassembly was conducted. As shown in FIG. 2h, no significant reduction in cell viability was observed in mSPAM-treated RAW264.7 macrophage cells at 24 h post-incubation. Therefore, it was confirmed that the mSPAM nanoassembly was nontoxic and safe for in-vitro and in-vivo investigations.

Figure 3:
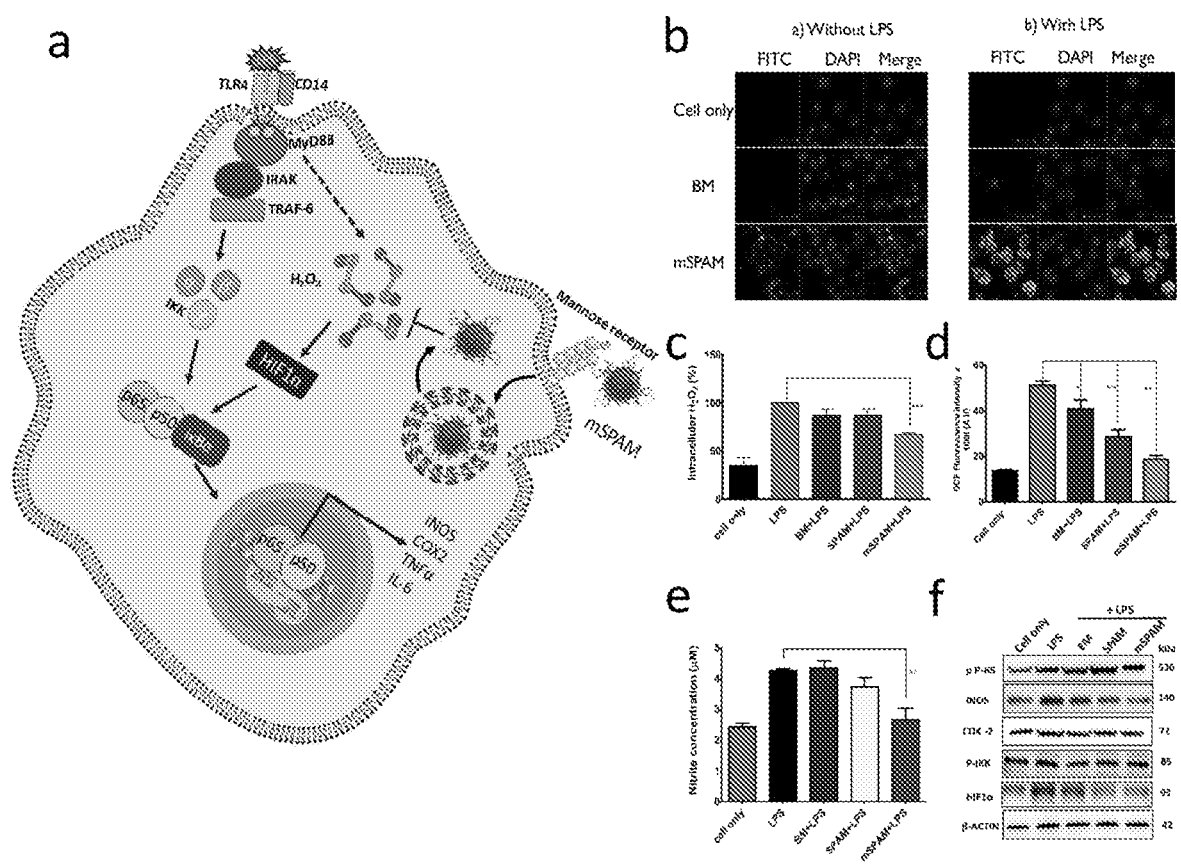
FIG. 3 shows a schematic representation of mSPAM nanoassembly alleviating LPS induced inflammatory protein expression in the RAW264.7 cell line (a); intracellular uptake results of mSPAM nanoassembly in RAW264.7 cells treated with and without LPS (b); a plot of intracellular $H_2O_2$ level in mSPAM nanoassembly treated LPS stimulated RAW264.7 cell line using PO assay (c); a plot of ROS level in mSPAM nanoassembly treated LPS-stimulated RAW264.7 cells using DCFDA assay (d); a plot of NO level in mSPAM nanoassembly treated LPS stimulated RAW264.7 cells (e); and western blot analysis of proteins in NF-κB pathway in RAW264.7 treated with mSPAM nanoassembly (f) (n=4, SEM, *p≤0.05, p≤0.01, and *p≤0.001)

Experimental Example 2: In-Vitro Experiment of Inflammation Activity Reduction by mSPAM Nanoassembly FIG. 3a shows the mechanism of anti-inflammation by mSPAM nanoassembly in lipopolysaccharide (LPS)-treated RAW264.7 macrophages. For effective therapeutic activity, the nanomaterials should efficiently enter the cells and generate the desired scavenging effect without noticeable toxicity. Hence, the intracellular uptake of mSPAM nanoassembly in the RAW264.7 cell line was investigated. The BM nanoparticle was conjugated with FITC fluorescent dye to visualize the cellular internalization of mSPAM nanoassembly.

As shown in FIG. 3b, the enhanced fluorescent intensity of the FITC-mSPAM nanoassembly was clearly noticed in RAW264.7 cells compared with FITC-BM nanoparticle-treated cells. Interestingly, the intracellular accumulation of FITC-mSPAM nanoassembly in LPS-treated RAW264.7 cells was markedly higher than in non-treated RAW264.7 cells. This clearly means that the mannosylated nanoassembly has enhanced intracellular uptake in LPS-stimulated RAW264.7 cells.

Meanwhile, it has been known that LPS increases the intercellular $H_2O_2$ level in macrophages. Therefore, the efficacy of mSPAM nanoassembly on the intercellular $H_2O_2$ level in LPS-treated macrophages was investigated in the present experiment.

As shown in FIG. 3c, macrophages treated with mSPAM nanoassembly displayed less production of intracellular $H_2O_2$ than did LPS-treated and (BM+LPS)-treated groups. Endotoxins induce the secretion of reactive oxygen species (ROS) through the TLR-4-mediated NADPH oxidase pathway. Elevated ROS levels mediated by the LPS/TLR4 signaling cascade in macrophages triggered the immune response through production of $H_2O_2$ by superoxide dismutase. Therefore, the efficacy of mSPAM nanoassembly in reducing the levels of ROS and $H_2O_2$ production in macrophage cells was investigated.

As shown in FIG. 3d, the LPS treatment of macrophages normally stimulated ROS production. However, the mSPAM nanoassembly significantly reduced ROS levels in LPS-treated cells compared with non-targeted SPAM or BM treated cells.

Inducible nitric oxide synthase (iNOS) induced by LPS-stimulated macrophages can accelerate the secretion of the inflammatory mediator nitric oxide (NO). Therefore, referring to FIG. 3e, further investigation of NO production in LPS-induced cells treated with mSPAM nanoassembly was performed. Levels of NO were greatly reduced in macrophages treated with mSPAM nanoassembly and were similar to those of negative control groups (cells without LPS treatment).

Then, expression patterns of P-IKK and pP-65 proteins responsible for the TLR-4-mediated NF-κB pathway in immune cells were investigated. The concentrations of the used LPS and mSPAM were 1 and 10 μg/mL, respectively. As shown in FIG. 3f, the mSPAM nanoassembly significantly reduced the expression of pP-65 proteins. Moreover, the expression of pro-inflammatory markers iNOS and COX-2 was highly suppressed after treating LPS-stimulated RAW 278 264.7 cells with mSPAM nanoassembly, although there was no significant change in p-IKK expression level in mSPAM nanoassembly treated RAW264.7 cells compared to the LPS control. Furthermore, HIF1α protein expression was significantly reduced by mSPAM nanoassembly compared to the LPS control. It has been reported that HIF1α activation induced the expression of pP-65. Based on these studies, it can be concluded that mSPAM nanoassembly did not stimulate the NF-κB/p-IKK pathway, whereas the mSPAM nanoassembly inhibited pP-65 expression through suppressing HIF1α expression by scavenging $H_2O_2$.

Experimental Example 3: In-Vivo Experiment of Inflammation Activity Reduction by mSPAM Nanoassembly As discussed in Experimental Example 2 above, the in-vitro investigation of the inflammation activity reduction effect by mSPAM nanoassembly was successfully confirmed. Thereafter, the therapeutic role of mSPAM nanoassembly in preventing LPS-induced $H_2O_2$ production in macrophages was investigated in a local inflammation mouse model.

L012 luminol agent shows luminescence only in the presence of ROS produced from $H_2O_2$ in LPS-injected tissues. Therefore, intraplantar injection of LPS was performed in both paws, and the mSPAM nanoassembly was subsequently injected in the same site after 4 h. The ROS levels in the paw site were visualized using L012 luminol dye at 4 h after sample injection.

Figure 4:
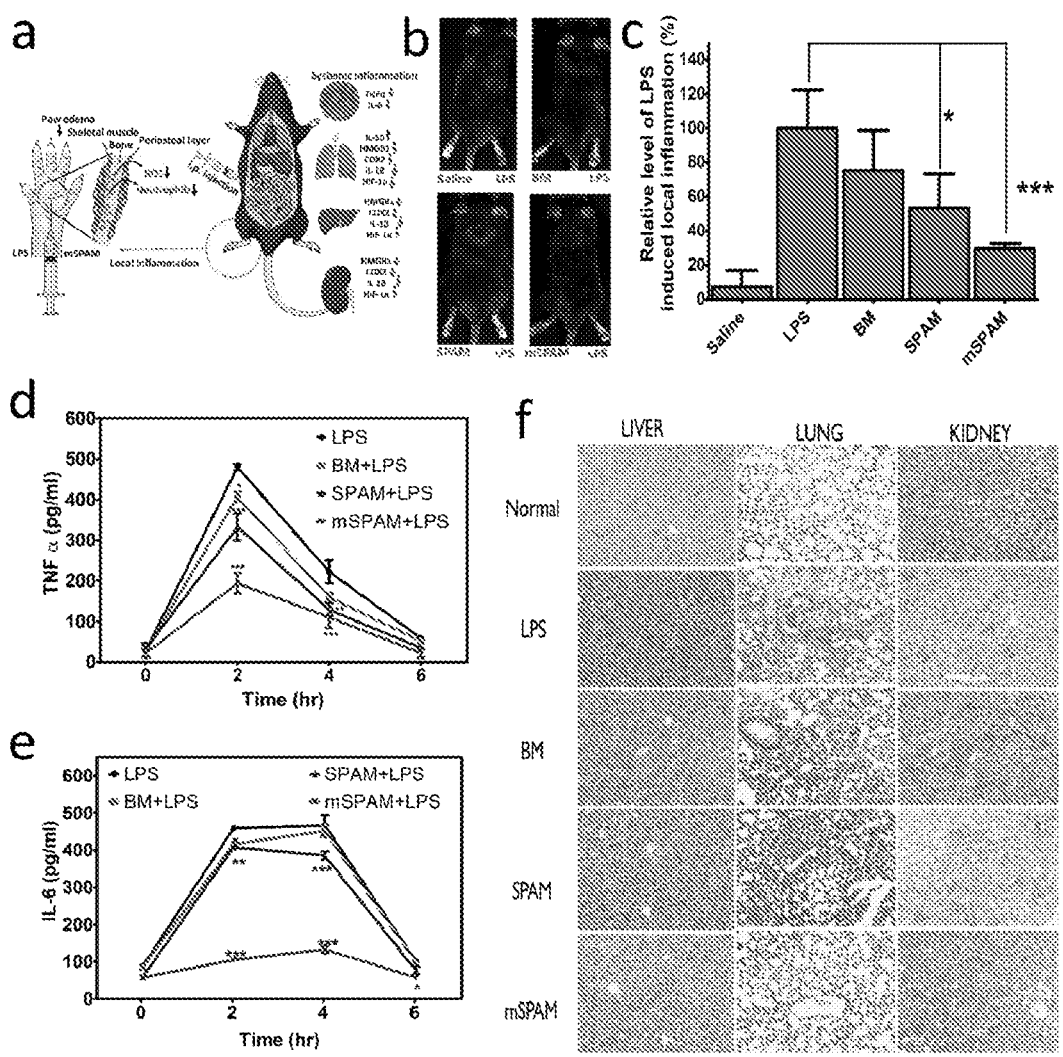
FIG. 4 shows local and systemic inflammation induction by LPS in C57BL/6 mice and local inflammation analysis in mouse paws injected with LPS (1 mg/kg) and mSPAM nanoassembly (25 mg/kg) using L012 luminol (a); luminescence images of the mSPAM nanoassembly treated mice (b); a plot of relative level of inflammation measured based on the luminescent intensity in the paw region (c); ELISA analysis of TNFα in serum (d); ELISA analysis of IL-6 level in serum (e); and histology of liver, lung, and kidney from LPS-induced mice treated with mSPAM nanoassembly (f) (n=6, SEM, *p≤0.05, p≤0.01, *p≤0.001)

As shown in FIG. 4b, mSPAM nanoassembly treatment reduced LPS-induced inflammation and neutrophils recruitment in mouse paws. As seen in FIGS. 4b and 4b, the injection of LPS alone in mouse paws showed higher L012 luminescent signals, whereas the signal was drastically lower in the mSPAM nanoassembly treatment group than in the BM- and SPAM-treated groups. This result is attributed to the successful catalysis of $H_2O_2$ secreted during inflammation by mSPAM nanoassembly and regulation of neutrophil infiltration in the paws.

During sepsis, LPS released from Gram-negative bacteria escalates the secretion of pro-inflammatory cytokines, such as TNFα and IL-6, in the circulation. C57BL/6 mice were injected with mSPAM nanoassembly (25 mg/kg) along with LPS (1 mg/kg) by I.P. injection. The levels of TNF-α and IL-6 were measured at 0, 2, 4, and 6 h after LPS injection. As shown in FIGS. 4d and 4e, respectively, LPS administration induced elevated production of TNF-α and IL-6 at 2 and 4 h post-injection. The co-administration of LPS along with mSPAM nanoassembly inhibited TNF-α production significantly at 2 and 4 h compared with the LPS-only treated group, whereas IL-6 production was reduced up to 73% and 72% at 2 and 4 h post-injection, respectively.

Referring to FIG. 4f, the histopathology of liver, lung, and kidney tissues isolated from the 24 h treatment groups were analyzed using H&E staining. In LPS-treated tissues, lung histology showed thickening of alveolar septa, pulmonary edema, neutrophil infiltration, and hemorrhage. Liver histology displayed infiltration of inflammatory cells into the cavities of liver tissues and vacuolar degeneration in LPS-treated mice. Referring to FIG. 4f, a loss of renal tubular epithelial cells, a decrease in brush borders, and a decrease in renal epithelial cells were clearly noticed on kidney histology.

Figure 5:
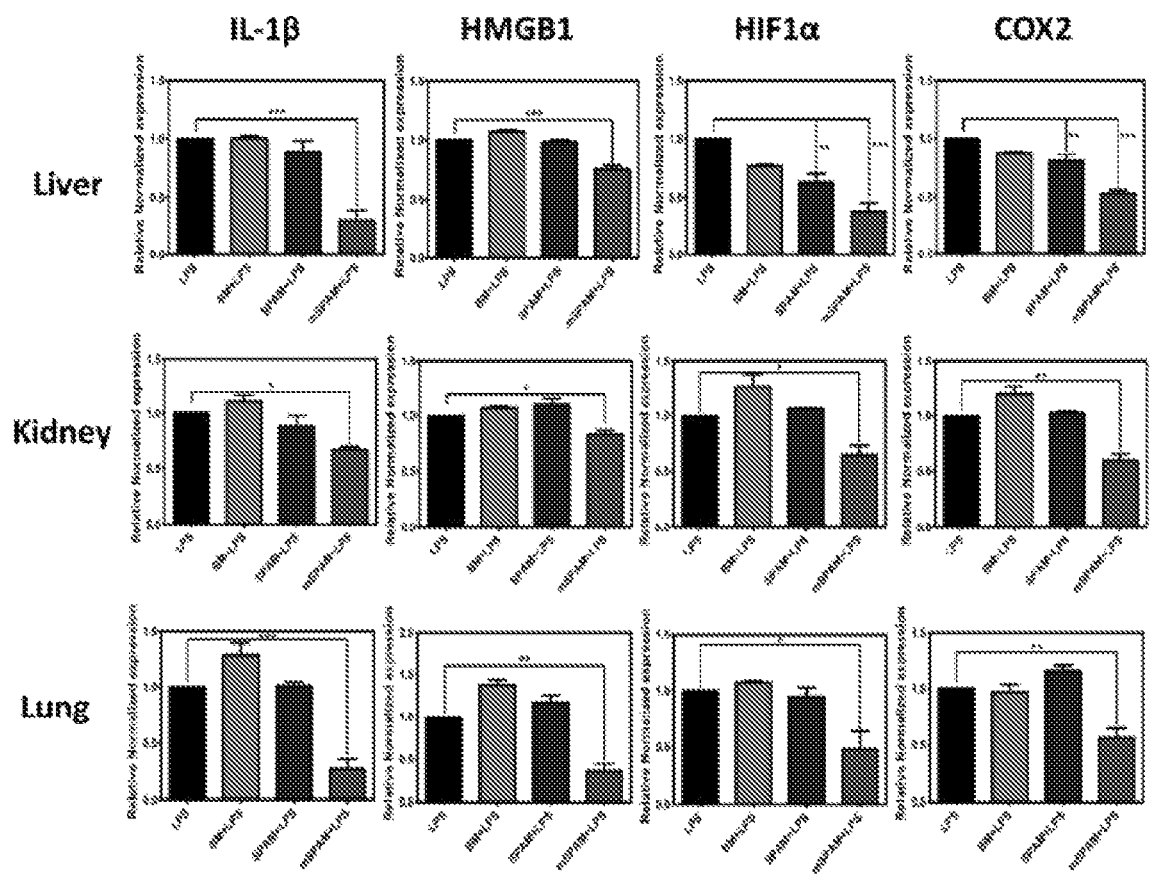
FIG. 5 shows gene expression assay results of IL-1β, HMGB1, HIF1α, and COX2 in liver, kidney, and lung isolated from mice.

Meanwhile, All these abnormalities were found to be absent in the mSPAM nanoassembly treatment group. Hence, further investigation was carried out to analyze the expression of pro-inflammatory genes, such as IL-1β, HMGB1, HIF1α, and COX2 in major organs, such as liver, kidney, and lung samples, isolated from treated mice. Referring to FIG. 5, mSPAM nanoassembly treatment showed a significant reduction in IL-1β, HIF1α, and COX2 transgene expression in the liver, lungs, and kidneys, compared with those from the LPS-treated group. However, the organs of the SPAM- or BM-treated animals did not show significant changes in terms of gene expression compared with LPS-treated animals. Meanwhile, secretory HMGB1 proteins are lethal mediators of LPS-induced systemic inflammation and are released by activated macrophages, further orchestrating the secretion of other pro-inflammatory cytokines, such as TNF-α and IL-6. As shown in FIG. 5, following LPS induction, treatment with mSPAM nanoassembly produced a significant reduction in gene expression of HMGB1 in the liver, lung, and kidneys, compared with BM- and SPAM-treated animals.

That is, it was confirmed that mSPAM nanoassembly treatment inhibited expression of pro-inflammatory proteins in the major organs, and therefore suppressed secretion of pro-inflammatory cytokines, such as TNF-α and IL-6, in the serum.

Figure 6:
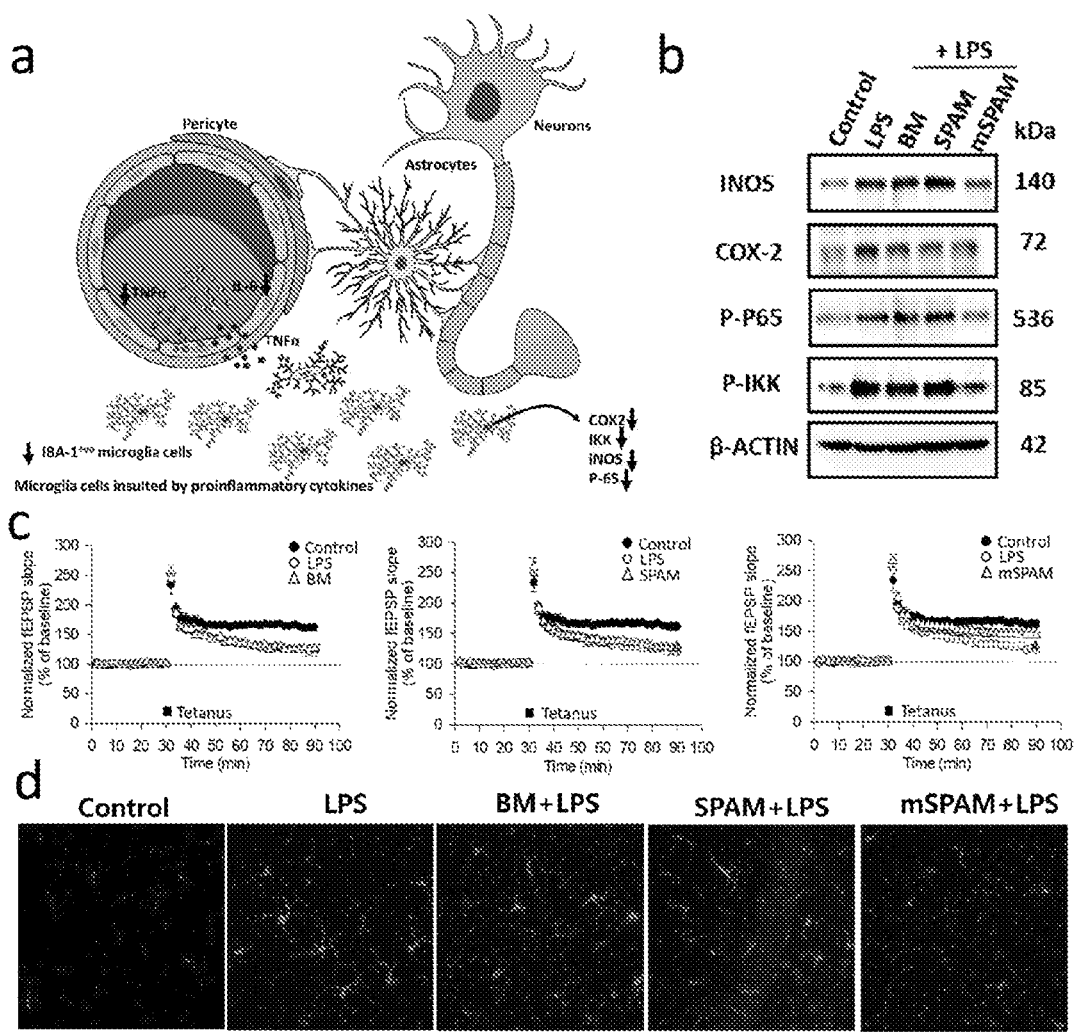
FIG. 6 shows a schematic representation of mSPAM nanoassembly (25 mg/kg) and its indirect role in alleviating neuroinflammation in LPS (1 mg/kg)-treated mice (a); western-blot analysis of inflammatory marker expression in brain tissue of mSPAM nanoassembly treated LPS induced mice (b); electrophysiological analysis of mSPAM nanoassembly treated LPS-induced mice brain (c); and IBA-1 fluorescence staining of mice brain (d).

It was previously confirmed that LPS administration increases blood levels of pro-inflammatory cytokines, such as TNFα and IL-6. Referring to FIG. 6a, elevated plasma levels of inflammatory cytokines, such TNF-α and IL-6, trigger immune activation in brain microglial cells, resulting in the induction of neuro-inflammatory disorders, such as Alzheimer's or Parkinson's disease. Furthermore, pro-inflammatory mediators, such as NOS, PGE2, and COX-2, are also activated by IL-6 and TNF-α in microglial cells. Referring to FIG. 6b, it can be seen that expression of NF-κB, COX-2, and iNOS increased in mice treated with LPS. Interestingly, the levels of these pro-inflammatory markers and pro-inflammatory marker were significantly reduced in SPAM-treated mice.

As shown in FIG. 6c, to evaluate the therapeutic efficiency of mSPAM nanoassembly in an LPS-induced neuroinflammation model, long-term potentiation (LTP) analysis through electrophysiological field recording was employed. The administration of LPS significantly impaired LTP (118.4±3) compared to the control (159.6±5). The co-administration of mSPAM nanoassembly with LPS significantly prevented or reversed LP-induced LTP impairment (149.3±3). However, such significance was not observed with BM or SPAM co-treatment.

As shown in FIG. 6d, IBA-1 immunostaining was performed to confirm whether systemic administration of mSPAM nanoassembly reduced the activation of microglial cells. FIG. 5d shows that administration of mSPAM nanoassembly effectively reduced activation of microglia cells to levels similar to that of the control group (mice without LPS treatment). Reactive microglia cells activate the major transcription factor nuclear factor κB (NF-κB) pathway and enhance expression of pro-inflammatory cytokines, COX-2 and iNOS, leading to neuroinflammation. Taken together, these data indicate that mSPAM nanoassembly attenuated LPS-induced neuroinflammation and promoted brain homeostasis.

The features, structures, effects, and the like described in the above-described embodiments include at least one embodiment of the present disclosure, but the present disclosure is not limited only to one embodiment. Further, the features, structures, effects, and the like illustrated in each embodiment may be combined or modified into other embodiments by those skilled in the art. Therefore, contents related to such combination or modification should be interpreted to be included in the scope of the disclosure.

In addition, the present disclosure has been particularly described with reference to exemplary embodiments, but the present disclosure is not limited thereto. It will be understood by those skilled in the art that various modifications and applications, which are not illustrated in the above, may be made without departing from the spirit and scope of the present disclosure. For example, respective elements specifically shown in the embodiments can be modified and implemented. It should be interpreted that differences related to such modifications and applications are included in the scope of the disclosure defined in the appended claims.

What is claimed is:

1. A macrophage-targeting nanoassembly, which is a mannosylated polymeric albumin manganese dioxide (mSPAM) nanoassembly.

2. The nanoassembly of claim 1, wherein the nanoassembly is formed by synthesis of a bovine serum albumin nanoparticle coated with manganese dioxide (BSA-MnO$_2$, BM) and mannosylated disulfide cross-linked polyethylenimine (ssPEI-Mannose, mSP).

3. The nanoassembly of claim 1, wherein the nanoassembly selectively removes hydrogen peroxide ($H_2O_2$) to suppress an inflammation inducing factor.

4. The nanoassembly of claim 1, wherein the nanoassembly alleviates lipopolysaccharide (LPS)-induced endotoxemia and neuritis.

5. A macrophage-targeting anti-inflammatory composition containing a mannosylated polymeric albumin manganese dioxide nanoassembly.

6. The anti-inflammatory composition of claim 5, wherein the nanoassembly is formed by synthesis of a bovine serum albumin nanoparticle coated with manganese dioxide (BSA-MnO$_2$, BM) and mannosylated disulfide cross-linked polyethylenimine (ssPEI-Mannose, mSP).

7. The anti-inflammatory composition of claim 5, wherein the nanoassembly selectively removes hydrogen peroxide (H$_2$O$_2$) to suppress an inflammation inducing factor.

8. The anti-inflammatory composition of claim 5, wherein the nanoassembly alleviates LPS-induced endotoxemia and neuritis.

9. A method of treating or reducing inflammatory diseases in a mammal in need thereof, said method comprising: administering a mannosylated polymeric albumin manganese dioxide (mSPAM) nanoassembly.

* * * * *